(12) United States Patent
Wild et al.

(10) Patent No.: US 6,936,345 B2
(45) Date of Patent: Aug. 30, 2005

(54) METHOD FOR PROVIDING FIBERS OR NON-WOVEN FABRIC WITH AN ANTI-MICROBIAL FINISH

(75) Inventors: Christine Wild, Hilden (DE); Raymond Mathis, Duesseldorf (DE); Edda Schirmer, Wuppertal (DE); Rolf Stein, Langenfeld (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 119 days.

(21) Appl. No.: 10/467,466
(22) PCT Filed: Jan. 30, 2002
(86) PCT No.: PCT/EP02/00921
§ 371 (c)(1),
(2), (4) Date: Aug. 8, 2003
(87) PCT Pub. No.: WO02/063090
PCT Pub. Date: Aug. 15, 2002

(65) Prior Publication Data
US 2004/0072489 A1 Apr. 15, 2004

(30) Foreign Application Priority Data
Feb. 8, 2001 (DE) .......................... 101 05 623

(51) Int. Cl.$^7$ ............................. D02G 3/00; B05D 3/00; B32B 5/02
(52) U.S. Cl. ....................... 428/375; 427/2.31; 442/123
(58) Field of Search ................................. 428/375, 394; 427/2.31; 442/123

(56) References Cited

U.S. PATENT DOCUMENTS

| 4,112,167 | A | | 9/1978 | Dake et al. |
| 5,045,387 | A | | 9/1991 | Schmalz |
| 5,962,663 | A | | 10/1999 | Wachter et al. |
| 6,190,736 | B1 | | 2/2001 | Mathis |
| 6,733,790 | B1 | * | 5/2004 | Garces Garces ............ 424/497 |
| 6,818,296 | B1 | * | 11/2004 | Garces Garces et al. 428/402.2 |

FOREIGN PATENT DOCUMENTS

| DE | 44 42 987 A1 | 6/1996 |
| DE | 195 37 001 A1 | 3/1997 |
| DE | 196 04 180 A1 | 8/1997 |
| EP | 0 395 099 B1 | 10/1990 |
| FR | 2 701 266 | 8/1994 |
| WO | WO 98/03716 | 1/1998 |
| WO | WO 99/32697 | 7/1999 |
| WO | WO 00/04230 | 1/2000 |

OTHER PUBLICATIONS

Skjak–Braek et al., "Chitin and Chitosan" 1989 Elsevier Science Publishers LTD., pp. 818–820, table 3 XP002205161.
Elvers et al., "Nonwoven Fabrics", Ullmann's Encyclopedia of Industrial Chemistry Fifth Edition, vol. A17, VCH Weinheim, 1994, pp. 572–581.
Gerhartz et al., "Chitin and Chitosan", Ullmann's Encyclopedia of Industrial Chemistry Fifth Edition vol. A6, Weinheim, Verlag Chémie, 1986, pp. 231–232.
Gesslein et al., "Chitosan a gift from the sea", HAPPI, 27, p. 57 and 59 (1990).
Oyvind Skaugrud, "Chitosan—New Biopolymer For Cosmetics & Drugs",Drug Cosm. Ind. 148, (1991) pp. 24,26,30.
Onsoyen et al., "Adding Benefits to Cosmetic Formulations by Tailormade Chitosans",Seifen–Ole–Fette–Wachse–117, (1991) pp. 633–637.
Sannan et al., "Studies on Chitin, 2", Makromol. Chem. 177, pp. 3589–3600.

* cited by examiner

Primary Examiner—N. Edwards

(57) ABSTRACT

A process for antibacterially finishing a polymeric substrate involving: (a) providing a polymeric substrate made from a compound selected from the group consisting of a polyolefin, a polyester, and combinations thereof; (b) providing an antibacterial finish composition containing: (i) from about 0.1 to 10% by weight of at least one monoester of glycerol and a $C_{6-14}$ fatty acid; and (ii) from about 0.01 to 10% by weight of chitosan, all weights being based on the weight of the composition; and (c) applying the composition onto the polymeric substrate.

18 Claims, No Drawings

METHOD FOR PROVIDING FIBERS OR NON-WOVEN FABRIC WITH AN ANTI-MICROBIAL FINISH

BACKGROUND OF THE INVENTION

This application is a 371 of PCT/EP02/00921 filed Jan. 30, 2002.

This invention relates to a process for the antibacterial finishing of fibers or nonwovens, which exclusively or predominantly contain polyolefins or polyesters, to fibers or nonwovens finished by this process and to the use of a combination of glycerol monoesters and chitosan for the antibacterial finishing of fibers.

In the manufacture of sanitary articles, such as diapers or sanitary napkins, absorbent materials are used to absorb aqueous liquids. In order to prevent direct contact with the absorbent material during wear and to increase comfort, the absorbent material is wrapped in a thin water-permeable nonwoven. The nonwovens used for this purpose are normally made of synthetic fibers, such as polyolefin or polyester fibers, because fibers such as these are inexpensive to produce, exhibit good mechanical properties and, in the case of polyolefins, can be heat-bonded. However, untreated polyolefin or polyester fibers are not suitable for this particular application because, in view of their hydrophobic surface, they are not sufficiently permeable to aqueous liquids. Accordingly, the fiber surface has to be made hydrophilic by a corresponding finish. It is also desirable that the hydrophilic finish of the fibers should remain intact for as long as possible without any reduction in the permeability to water of the nonwoven. Accordingly, another problem arises out of the fact that the nonwovens used in sanitary articles are in direct contact with the skin and, hence, are exposed to significant bacterial contamination. Known spin finishes, which provide fibers the required hydrophilic finish, generally have no antibacterial activity so that, in unfavorable circumstances, for example in environments with high moisture levels, considerable bacterial growth can occur on the surface of the nonwoven. In cases of slight damage to the skin surface for example, this can lead to inflammation of the skin which should be avoided.

Hydrophilic finishing of fibers of the type under discussion is known from the prior art. U.S. Pat. No. 5,045,387, for example, describes a formulation for the hydrophilic finishing of polyolefin fibers which contains a mixture of an alkoxylated ricinoleic acid derivative, a hydrogenated ricinoleic acid derivative, a $C_{18}$ fatty acid and a polyalkoxylated polymethyl siloxane. EP 395 099 A2 describes absorbent materials, more particularly tampons of rayon or polyester fibers, which are finished with glycerol monolaurate as a bacteriostatic toxin-inhibiting component. However, there is no reference to hydrophilic finishing of the fibers. WO 98/03716 proposes a combination of glycerol monoesters and alkyl polyglycosides for the hydrophilic finishing of fibers or nonwovens. However, nowhere in this document is there any reference to the problem of bacterial contamination.

The problem addressed by the present invention was to finish nonwovens in such a way that they would meet requirements in regard to the permanence of the hydrophilic finish and, in particular, would be capable of effectively suppressing the growth of harmful bacteria. The problem as stated is solved by the combination of antibacterial substances known per se with chitosan.

BRIEF SUMMARY OF THE INVENTION

In a first embodiment, the present invention relates to a process for the antibacterial finishing of fibers which exclusively or predominantly contain polyolefins or polyesters or nonwovens predominantly containing such fibers, characterized in that the fibers or nonwovens are treated with a water-based composition containing a) between 0.1 and 10% by weight, based on the total weight of the composition, of at least one monoester of glycerides and a $C_{6-14}$ fatty acid and
b) 0.01 to 10% by weight, based on the total weight of the composition, of chitosans and optionally other ingredients.

The process according to the invention is suitable for fibers which exclusively or predominantly, i.e. more than 50% by weight of which, contain polyolefins or polyesters, and for nonwovens which predominantly contain fibers such as these, fibers exclusively containing polyolefins or polyesters being preferred. Nonwovens containing 100% by weight of polyolefin or polyester fibers are particularly suitable.

DETAILED DESCRIPTION OF THE INVENTION

Polyolefin fibers are among the most commonly used fibers for the production of nonwovens. Examples of suitable polyolefins are polypropylene, polyethylene or copolymers of ethylene or propylene with butadiene. Polyester fibers, mainly polyethylene terephthalate fibers, are also used. Besides the fibers mentioned, other synthetic fibers suitable for the production of nonwovens may also be used, including for example fibers of Nylon®. Fibers consisting of two or more components, for example polyester/copolyester fibers or polypropylene/ polyethylene fibers, are also particularly suitable.

The nonwovens used in the process according to the invention may be produced by any of the known processes for producing nonwovens which are described, for example, in Ullmann's Encyclopedia of Industrial Chemistry, Vol. A 17, VCH Weinheim 1994 pages 572–581. Nonwovens produced either by the dry laid process or by the spunbonded process are preferred. The dry laid process starts out from staple fibers which are normally separated by carding into individual fibers and are then laid together by an aerodynamic or hydrodynamic process to form the unbonded nonwoven. The semi-finished nonwoven thus produced is then made up into the final nonwoven by a heat treatment known as thermobonding. To this end, the synthetic fibers are either heated to such an extent that their surface melts and the individual fibers are joined together at their points of contact or the fibers are coated with an additive which melts during the heat treatment, thus joining the individual fibers to one another. The bonds between the individual fibers are fixed by cooling. Besides this process, any of the other processes known for bonding nonwovens may of course also be used.

By contrast, the spunbonded process starts out from individual filaments which are formed by melt spinning from extruded polymers which are forced under high pressure through spinning jets. The filaments emerging from the spinning jets are bundled, stretched and laid to form a nonwoven which, normally, is then thermobonded.

The process according to the invention is particularly suitable for nonwovens produced by the spunbonded process or by the dry laid process.

In the process according to the invention, the fibers or nonwovens are treated with a finish containing at least one monoester of glycerol and a $C_{6-14}$ fatty acid and chitosan. This water-based finish is applied to the untreated nonwoven or to the fibers by the process according to the invention. Any of the methods and machines typically used in the textiles industry, for example a padding machine, may be used for this purpose. However, spray application, roller application or stick application may also be used. The process according to the invention is preferably designed in such a way that the fibers or nonwovens receive an add-on of finish, based on active substance, in a quantity of 0.3 to 2.0% by weight, preferably in a quantity of 0.25 to 1.5% by weight and more particularly in a quantity of 0.4 to 0.8% by weight, based on the weight of the fibers or nonwovens. The fibers or nonwovens are then dried and further processed. The water-based compositions themselves are formulated as a solution or emulsion, the monoglycerides having an emulsifying effect.

The water-based compositions used in the process according to the invention contain at least one monoester of glycerol and a $C_{6-14}$ fatty acid. The percentage monoglyceride content is at least 0.1% by weight, based on the total weight of the composition. 10% by weight may be regarded as the upper limit. The compositions used in the process according to the invention preferably contain the monoglycerides in quantities of 0.1 to 1.0% by weight. The fatty acid glycerides should be highly pure, i.e. they should have a low percentage content of diesters or triesters of glycerol and fatty acid. Mixtures of various monoglycerides may also be used. Suitable fatty acids are, for example, caproic, caprylic, capric, lauric and myristic acid. A preferred ester is the monoester of glycerol and lauric acid, glycerol monolaurate. The water content of the compositions is 99% by weight and may be reduced to 10% by weight. However, the water content is preferably in the range from 99 to 80% by weight and more particularly in the range from 99 to 95% by weight. Deionized water or osmosis water is preferably used.

A second essential ingredient of the finishes according to the invention is chitosan. Chitosans are biopolymers which belong to the group of hydrocolloids. Chemically, they are partly deacetylated chitins differing in their molecular weights which contain the following—idealized—monomer unit:

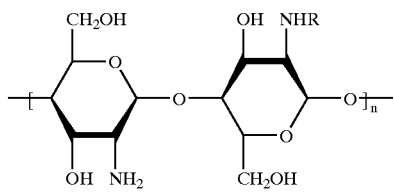

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations (cf. Ullmann's Encyclopedia of Industrial Chemistry, 5th Ed., Vol. A6, W inheim, Verlag Chemi, 1986, pages 231–232). Overviews of this subject have also been published, for example, by B. Gesslein et al. in HAPPI 27, 57 (1990), 0. Skaugrud in Drug Cosm. Ind. 148, 24 (1991) and E. Onsoyen et al. in Seifen-Öle-Fette-Wachse 117, 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, demineralized by addition of mineral acids and, finally, deacetylated by addition of strong bases, the molecular weights being distributed over a broad spectrum. Corresponding processes are known, for example, from Makromol. Chem. 177, 3589 (1976) or French patent application FR 2701266 A. Preferred types are those which are disclosed in German patent applications DE 4442987 A1 and DE 19537001 A1 and which have an average molecular weight of 10,000 to 5,000,000 dalton, preferably 10,000 to 500,000 dalton and more particularly 800,000 to 1,200,000 dalton and/or a Brookfield viscosity (1% by weight in glycolic acid) below 5,000 mPas, a degree of deacetylation of 80 to 88% and an ash content of less than 0.3% by weight. Chitosans with an average molecular weight of 10,000 to 5,000,000 dalton are normally used. A preferred embodiment is characterized by the use of chitosans with a molecular weight of 40,000 to 500,000 dalton. However, chitosans with a molecular weight of 50,000 to 100,000 dalton are particularly preferred. Besides the chitosans as typical cationic biopolymers, anionically or nonionically derivatized chitosans such as, for example, the carboxylation, succinylation or alkoxylation products described, for example, in German patent application DE 19604180 A1 are also suitable for the purposes of the invention.

The quantity of chitosan used in the compositions used in accordance with the invention is in the range from 0.01 to at most 10% by weight, based on the water-containing composition. Preferred ranges are from 0.5 to 5% by weight and while particularly preferred ranges are from 1.0 to 2.5% by weight.

Besides the above-described compounds a) and b), other known textile auxiliaries may be used in the compositions including, for example, antistatic agents or lubricants and pH adjusters, lubricants, antistatic agents, emulsifiers and skin protection additives, for example aloe vera or bisabolenes. These auxiliaries are normally used in quantities of at most 20% by weight, based on the total weight of the compositions. Quantities of 0.1 to 10% by weight and more particularly 1.0 to 5.0% by weight are preferred. The compositions used in accordance with the invention have a pH of 4 to 7 and preferably in the mildly acidic range, i.e. from pH 5 to 6.

It can also be of advantage to design the process according to the invention in such a way that the nonwoven is treated with a finish which, besides the components already described, also contains quaternary esteramine compounds corresponding to formula (I):

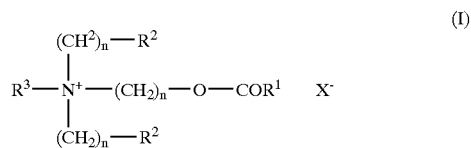

in which $COR^1$ is an aliphatic acyl group containing 12 to 22 carbon atoms and 0, 1, 2 or 3 double bonds, $R^2$ is H or OH and $R^3$ is an alkyl group containing 12 to 22 carbon atoms or preferably a group $(CH_2)_n$—O—$COR^1$, where n has a value of 1, 2 or 3 and X is either a halide, methosulfate, methophosphate or phosphate ion, in quantities of 0.5 to 2.5% by weight, based on the total quantity of the water-based composition.

The compositions used in accordance with the invention are preferably prepared by simply stirring the ingredients at room temperature (21° C.). However, higher temperatures, for example in the range from 40 to 90° C., may also be used in the preparation of the compositions, depending on the raw materials used.

In another embodiment, the present invention relates to antibacterially finished fibers exclusively or predominantly containing polyolefins or polyesters or to nonwovens predominantly containing such fibers which have been produced by the process according to the invention. Besides antibacterial properties, the fibers or nonwovens also show hydrophilic properties which they preferably retain even after repeated wetting. In particular, the nonwovens produced in accordance with the invention have liquid strike-through times of less than 10 seconds and, more particularly, less than 5 seconds. In the context of the present invention, liquid strike-through times are understood to be the times which a certain quantity of water or synthetic urine takes to pass through the nonwoven to an absorbent underlayer. This time is determined by EDANA Method No. 150.0-0-84 (EDANA=European Association of Nonwoven Manufacturers). For use in diapers or similar sanitary articles, the liquid strike-through time should be as short as possible in order to guarantee rapid transport of the liquid through the nonwoven to the absorbent material. In this way, the surface of the nonwoven remains dry and thus leads to increased wearing comfort. The nonwovens produced in accordance with the invention retain this favorable property, even after repeated use, and are further distinguished by the fact that, when the liquid strike-through time is determined by EDANA Method No. 150.0-8 preferably three times and more preferably five times in succession, they always have a liquid strike-through time of less than 10 seconds and, more particularly, less than 5 seconds.

The present invention also relates to sanitary articles, more particularly for feminine hygiene, such as diapers, tampons, panty liners or even wipes which contain nonwovens produced in accordance with the invention. The nonwovens produced in accordance with the invention are distinguished by a broad antibacterial action spectrum against *Staphylococcus aureus* and *Klebsiella pneumonia*. The latter are responsible for pneumonia and inflammation of the urinary tract and occur frequently in elderly people who are incontinent and, accordingly, have to use corresponding products for hygiene.

EXAMPLES

To measure the antibacterial properties of the nonwovens produced in accordance with the invention, 20 g/m² spun-bonded nonwovens were sprayed with four different finishes (see Table 1). An untreated nonwoven was tested for comparison. The spunbonded nonwovens were sprayed with an aqueous emulsion of the finish and then air-dried for 24 hours at room temperature. The nonwovens were then placed on a bacteria-containing nutrient substrate (standard agar). After incubation for 48 hours at 37° C., the growth under the nonwoven was evaluated. The results are set out in Table 1. Stantex S 6327 is a Cognis product which contains a combination of castor oil ethoxylates with PEG diesters. Hydagen CMF is an aqueous chitosan solution available from Cognis which contains chitosan with a molecular weight in the range from 50,000 to 100,000.

TABLE 1

| | | Growth under filter | |
|---|---|---|---|
| | Add-on [%] | *Staphylococcus aureus* | *Klebsiella pneumoniae* |
| GML + lauric acid (99/1) | 1 | No | Yes |
| GML/Stantex S 6327 | 1 | No | Yes |
| GML/Hydagen CMF | 1 | No | No |
| Untreated | — | Yes | Yes |

It can be seen that only product 1 according to the invention, i.e. glycerol monolaurate (GML) in combination with chitosan (Hydagen CMF), has an inhibiting effect both against *Staphylococcus aureus* and against *Klebsiella pneumoniae*. The combination of GML and lauric acid is only effective against *Klebsiella pneumoniae*. The combination of GML with Stantex S 6327 is effective against *Staphylococcus aureus* but not against *Klebsiella pneumoniae*. Only the claimed combination of glycerol monoesters with chitosans according to the invention has the desired effect against all relevant germs by which nonwovens are bacterially challenged.

What is claimed is:

1. A process for antibacterially finishing a polymeric substrate comprising:
   (a) providing a polymeric substrate made from a compound selected from the group consisting of a polyolefin, a polyester, and combinations thereof;
   (b) providing an antibacterial finish composition containing:
      (i) from about 0.1 to 10% by weight of at least one monoester of glycerol and a $C_{6-14}$ fatty acid; and
      (ii) from about 0.01 to 10% by weight of chitosan, all weights being based on the weight of the composition; and
   (c) applying the composition onto the polymeric substrate.

2. The process of claim 1 wherein the polymeric substrate is selected from the group consisting of fibers, non-wovens, and combinations thereof.

3. The process of claim 1 wherein the chitosan is present in the composition in an amount of from about 0.5 to 2% by weight, based on the weight of the composition.

4. The process of claim 1 wherein the monoester is glycerol monolaurate.

5. The process of claim 1 wherein the chitosan has a molecular weight of from about 30,000 to 1,000,000 dalton.

6. The process of claim 1 wherein the chitosan has a molecular weight of from about 40,000 to 500,000 dalton.

7. The process of claim 1 wherein the chitosan has a molecular weight of from about 50,000 to 100,000 dalton.

8. The process of claim 1 wherein the composition is applied onto the substrate in an amount of from about 0.2 to 2% by weight, based on the weight substrate.

9. The process of claim 1 wherein the composition is applied onto the substrate in an amount of from about 0.25 to 1.5% by weight, based on the weight substrate.

10. A polymeric substrate coated with an antibacterial composition comprising:
    (a) from about 0.1 to 10% by weight of at least one monoester of glycerol and a $C_{6-14}$ fatty acid; and (b) from about 0.01 to 10% by weight of chitosan, all weights being based on the weight of the composition.

11. The substrate of claim 10 wherein the polymeric substrate is select from the group consisting of fibers, non-wovens, and combinations thereof.

12. The substrate of claim 10 wherein the chitosan is present in the composition in an amount of from about 0.5 to 2% by weight, based on the weight of the composition.

13. The substrate of claim 10 wherein the monoester is glycerol monolaurate.

14. The substrate of claim 10 wherein the chitosan has a molecular weight of from about 30,000 to 1,000,000 dalton.

15. The substrate of claim 10 wherein the chitosan has a molecular weight of from about 40,000 to 500,000 dalton.

16. The substrate of claim 10 wherein the chitosan has a molecular weight of from about 50,000 to 100,000 dalton.

17. The substrate of claim 10 wherein the composition is present on the substrate in an amount of from about 0.2 to 2% by weight, based on the weight substrate.

18. The substrate of claim 10 wherein the composition is present on the substrate in an amount of from about 0.25 to 1.5% by weight, based on the weight substrate.

* * * * *